United States Patent [19]

Sarantakis

[11] 4,209,426
[45] Jun. 24, 1980

[54] POLYPEPTIDES RELATED TO SOMATOSTATIN

[75] Inventor: Dimitrios Sarantakis, West Chester, Pa.

[73] Assignee: American Home Products Corporation, New York, N.Y.

[21] Appl. No.: 42,843

[22] Filed: May 29, 1979

[51] Int. Cl.$^2$ ............... C07C 103/52; A61K 37/00
[52] U.S. Cl. ............... 260/8; 260/112.5 S; 424/177
[58] Field of Search ............... 260/172.5 S, 8; 424/177

[56] References Cited

U.S. PATENT DOCUMENTS

| 4,061,608 | 12/1977 | Sarantakis | 260/112.5 S |
| 4,077,952 | 3/1978 | Sarantakis | 260/112.5 S |
| 4,098,782 | 7/1978 | Sarantakis | 260/112.5 S |
| 4,104,267 | 8/1978 | Sarantakis | 260/112.5 S |

Primary Examiner—Delbert R. Phillips

Attorney, Agent, or Firm—Richard K. Jackson

[57] ABSTRACT

Polypeptides of the formula:

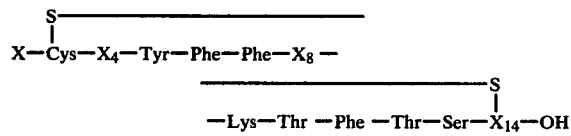

and the reduced linear form thereof, wherein
X is H, Ala-Gly-, Ala-D-Ala, Gly-Gly-Gly-, acetyl or benzoyl;
$X_4$ is Arg or His;
$X_8$ is Trp or D-Trp;
$X_{14}$ is Cys or D-Cys, or a non-toxic acid addition salts thereof, inhibit the secretion of growth hormone, insulin and glucagon.

7 Claims, No Drawings

POLYPEPTIDES RELATED TO SOMATOSTATIN

Somatostatin is the cyclic disulfide tetradecapeptide of the formula:

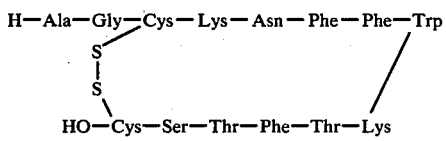

This peptide (I) has been identified as the "somatotropin-release inhibiting factor" (SRIF) which is secreted by the hypothalamus and regulates the secretion of pituitary growth hormone (GH) (somatotropin). [See Brazeau et al., *Science*, 179, 77 (1973), Burgus et al., *Proc. Nat. Acad. Sci.* (*USA*), 70, 684 (1973), and Ling et al., *Biochemical and Biophysical Res. Communication*, 50, 127 (1973)]. The reduced form of somatostatin (RS) is the linear tetradecapeptide of the formula:

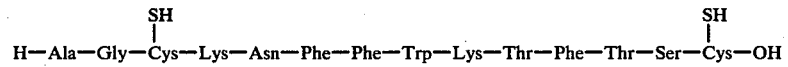

The reduced form (II) has been prepared by total synthesis, [see Rivier et al., *C. R. Acad. Sci. Ser. p. Sci. Natur.* (Paris), 276 2737 (1973) and Sarantakis and McKinley, *Biochem. and Biophys. Res. Communications*, 54, 234 (1973)] and it (II) can be converted to somatostatin (I) by oxidation whereby a bridging bond is formed between the two sulfhydryls of the two cysteinyl amino acid residues in the tetradecapeptide.

Various polypeptides which may be regarded as structural modifications of somatostatin have been prepared synthetically and are reported in the chemical literature. Such polypeptides have certain structural features in common with somatostatin and differ from somatostatin in that specific amino acid residues or functional groups originally present in the somatostatin molecule are either missing or are replaced by other amino acid residues or functional groups. The present invention relates to novel synthetic biologically active polypeptides which may be regarded as a structural modification of somatostatin. The polypeptides of the invention differ from somatostatin in the following respects: (a) the amino acids attached to Cys[2] are of varied identity including Ala[1]-Gly[2]-; (b) the Lys[4] residue is replaced by Arg or His; (c) the Asn[5] residue is replaced by Tyr; (d) the Trp[8] residue is either present or is replaced by D-Trp; and (e) the Cys[14] residue is either present or replaced by D-Cys. Modifications of somatostatin missing the Ala[1]-Gly[2] segment are reported by Rivier et al., *J. Med. Chem.*, 18, 123 (1975). Replacement of the Trp[8] residue by D-Trp is discussed by Rivier et al., *Biochem. Biophys. Res. Commun.*, 65, 746 (1975). Modifications of somatostatin wherein the Lys[4]-Asn[5] segment are replaced with other amino acid residues are disclosed in Belgian Pat. No. 839,405.

The invention sought to be patented comprises a chemical compound of Formula III:

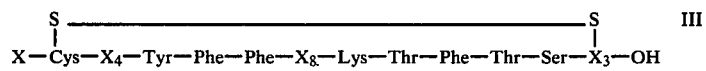

wherein
X is H, Ala-Gly-, Ala-D-Ala, Gly-Gly-Gly-, acetyl or benzoyl;
$X_4$ is Arg or His
$X_8$ is Trp or D-Trp;
$X_4$ is Cys or D-Cys;
or a non-toxic acid addition salt thereof.

In addition the invention contemplates the linear form of the compounds of Formula III, i.e. the non-cyclic reduced compounds of Formula IV which contain two free sulfhydryl groups; or a non-toxic acid addition salt thereof.

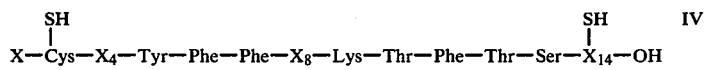

All optically active amino acids herein described and all amino acid residues in the polypeptides of Formula III and IV and the other polypeptides herein described are in the natural or L-configuration, unless otherwise indicated.

The compounds of Formula III and the linear reduced form thereof (Formula IV) inhibit the secretions of growth hormone, glucagon and insulin, and therefore, are useful in treatment of diabetes, acromegaly and other dysfunctions characterized by abnormal blood levels of those hormones. The compounds can be administered either alone or in combination with insulin where increased insulin blood levels are desired.

In general, the polypeptides of this invention are produced by the well known solid phase method as described by Stewart et al., Solid Phase Peptide Synthesis, Freeman and Co., San Francisco, 1969. As applied to the compounds of this invention, α-amino and sulfhydryl protected cysteine or D-cysteine is attached to a chloromethylated polystyrene resin and the α-amino protecting group is then removed with trifluoroacetic acid in methylene chloride, trifluoroacetic acid alone or hydrogen chloride in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent, protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., *Analyt. Biochem.*, 34, 595 (1970). Where incomplete coupling has occurred, the reaction is repeated before the α-amino protecting group is removed for introduction of the next amino acid sequence. Diisopropylcarbodiimide was employed as the coupling reagent.

After the desired amino acid sequence has been synthesized, the polypeptide is removed from the resin support by treatment with hydrogen fluoride and anisole to obtain the fully deprotected linear polypeptide. The cyclic disulfide is produced by oxidation, such as by treatment with $K_3Fe(CN)_6$ or by contact with air.

Non-toxic acid addition salts of the linear and cyclic polypeptides are produced by methods well known in the art from organic or inorganic acids which are non-toxic and acceptable for pharmaceutical purposes, such as hydrochloric, hydrobromic, sulfuric, phosphoric, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The processes of the invention are illustrated in the following Examples:

EXAMPLE 1 tert-Butyloxycarbonyl-S-p-methoxybenzyl-L-cysteinyl-$N^{im}$-tosyl-L-histidyl-O-2,6-dichlorobenzyl-L-tyrosyl-L-phenylalanyl-L-phenylalanyl-D-tryptophyl-$N^\epsilon$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl polystyrene ester Chloromethylated polystyrene resin was esterified with Boc-Cys(SMBzl)-OH according to Gisin, *Helv. Chim. Acta*, 56, 1976 (1973) and the polymeric ester was treated according to Schedule A for the incorporation of Boc-Ser(Bzl)-OH, Boc-Thr(Bzl)-OH, Boc-Phe-OH, Boc-Thr(Bzl)-OH, Boc-Lys(ClZ)-OH, Boc-D-Trp-OH, Boc-Phe-OH, Boc-Phe-OH, Boc-Tyr(Cl₂Bzl)-OH, Boc-His(Tos)-OH, and Boc-Cys(SMBzl)-OH to afford the title peptidoresin.

Schedule A: (for treatment of the resin ester)
1. Wash with methylene chloride ($CH_2Cl_2$), three times.
2. Treat with trifluoroacetic acid-methylene chloride (1:1, v/v) containing 5% 1,2-ethane dithiol for 5 minutes.
3. Repeat Step 2 for 25 minutes.
4. Wash with $CH_2Cl_2$, three times.
5. Wash with dimethylformamide (DMF).
6. Treat with 12% triethylamine in DMF for 3 minutes.
7. Wash with DMF.
8. Wash with $CH_2Cl_2$, three times.
9. Treat with 4 equivalents of the appropriate protected amino acid in $CH_2Cl_2$-DMF and stir for 5 minutes.
10. Add in two portions over a 30 minute period; 5 equivalents of diisopropylcarbodiimide dissolved in $CH_2Cl_2$. Allow reaction to procede for 6 hours.
11. Wash with DMF, three times.
12. Wash with $CH_2Cl_2$, three times.
13. Test by ninhydrin reaction according to the procedure of Kaiser et al., *Annal. Biochem.*, 34, 595 (1970). In case of incomplete reaction, repeat Steps 9 to 13, as above.

EXAMPLE 2

L-Cysteinyl-L-histidyl-L-tyrosyl-L-phenylalanyl-L-phenylalanyl-D-tryptophyl-L-lysyl-L-threonyl-L-phenylalanyl-L-threonyl-L-seryl-L-cysteine cyclic (1-12) disulfide diacetate salt The peptidoresin of the previous example (9 g.) was mixed with anisole 18 ml. and treated with ca. 200 ml. liquid HF with exclusion of air in an ice bath for 60 minutes after which time the excess HF was removed under vacuo, and the residue taken in 2N aqueous AcOH. The mixture was filtered, the filtrate was washed with ether and the aqueous layer was poured into 5 liters of deaerated water. The pH of the solution was adjusted to 7.1 with $NH_4OH$ and the disulfhydryl compound was oxidized to the disulfide with $K_3Fe(CN)_6$. The pH was adjusted to 5 with glacial AcOH and the solution was treated with Bio Rad Ag3-X4A (Cl form), anion exchange resin and filtered. The peptidic material in the filtrate was absorbed onto Amberlite CG-50 ($H^+$ form) and then eluted with a mixture of water-pyridine-glacial acetic acid, 66:30:4, v/v. The fractions containing the peptidic material were pooled and lyophilized to yield 308 mg. of crude compound.

Amino acid analysis: Thr(2) 1.47, Ser(1) 0.19, Cys(2) 1.47, Tyr(1) 0.75, Phe(3) 3.01, Lys(1), 1, His(1) 0.83, Trp N.D.

The above crude product was chromatographed through a column of Sephadex G25 (2.5 × 94 cm) and eluted with 10% aqueous AcOH. The material which emerged in fractions 87-101 (ca. 5 ml. each) was pooled and lyophilized to yield the title dodecapeptide (132 mg.).

TLC, Avicel precoated glass plates, chlorox-tolidine spray Rf (BWA, 4:1:1, v/v) 0.50 Rf (tert. AmOH, W, P, 7:6:7, v/v) 0.78.

Amino acid analysis: Thr(2) 1.91, Ser(1) 0.97, Cys(2) 1.62, Tyr(1) 0.96, Phe(3) 3, Lys(1) 1.04, His(1) 0.88, Trp(1) 0.83.

EXAMPLE 3

L-Cysteinyl-L-arginyl-L-tyrosyl-L-phenylalanyl-L-phenylalanyl-D-tryptophyl-L-lysyl-L-threonyl-L-phenylalanyl-L-threonyl-L-seryl-L-cysteine cyclic (1-12) disulfide triacetate salt The compound was prepared in a fashion similar to the previous example.

TLC, Avicel precoated glass plates, chlorox-tolidine spray, Rf (BWA, 4:1:1, v/v) 0.40, Rf (tert. AmOH, W, P; 7:6:7, v/v) 0.80.

Amino acid analysis: Thr(2) 1.85, Ser (1) 0.82, Cys(2) 1.63, Tyr(1) 0.81, Phe(3) 3, Lys(1) 1.02, Arg(1) 0.93, Trp N.D.

The biological activity of the products of the preceding preparatory examples were determined by the following procedure:

Albino male rats were administered Nembutal intraperitoneally at a dose of 50 milligrams per kilogram. Fifteen minutes later a subcutaneous injection of the test compound of physiological saline was administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot was assayed for growth hormone (GH), insulin and glucagon by radio immunoassay. The results of the assay are as follows:

| Compound | Dose µg/kg. | GH ng/ml. | INS µU/ml. | GLUN pg/ml. |
|---|---|---|---|---|
| Control | — | 268 ± 46 | 323 ± 28 | 379 ± 109 |
| Example 2 | 200 | 68 ± 14* | 254 ± 38 | 58 ± 24+ |
| Control | — | 407 ± 62 | 271 ± 44 | 46 ± 72 |
| Example 3 | 200 | 101 ± 24* | 59 ± 16* | 13 ± 3* |
| Control | — | 202 ± 11 | 238 ± 23 | 86 ± 6 |
| Example 3 | 50 | 80 ± 16* | 85 ±14* | 12 ± 4* |
| Control | — | 335 ± 33 | 309 ± 31 | 52 ± 10 |
| Example 3 | 10 | 207 ± 29 | 278 ± 36 | 12 ± 4* |

*p <0.01
+p <0.05

These data show that the compounds of Examples 2 and 3, representative of the other compounds of the invention, are effective agents for reducing secretion of growth hormone, glucagon, and insulin levels at a dose as low as 50 micrograms per kilogram, with selectivity of action toward glucagon at a dose as low as 10 micrograms per kilogram.

The compounds described herein may be administered to warm-blooded mammals, either intravenously, subcutaneously, intramuscularly, or orally to control serum glucose in the treatment of diabetes. The required dosage will vary with the particular condition being treated, the severity of the condition and the duration of treatment.

The active ingredient may be administered alone or in combination with pharmaceutically acceptable carriers or excipients. Suitable pharmaceutical compositions will be apparent to those skilled in the art.

What is claimed is:

1. A polypeptide of the formula:

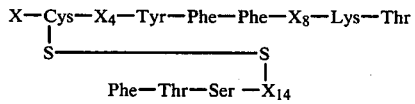

its linear precursor or a non-toxic acid addition salt thereof, in which:

X is hydrogen, Ala-Gly, Ala-D-Ala, Gly-Gly, Gly-Gly-Gly, lower alkanoyl or benzoyl;

$X_4$ is Arg or His;

$X_8$ is L-Trp or D-Trp;

and $X_{14}$ is Cys or D-Cys.

2. A polypeptide of claim 1 of the formula:

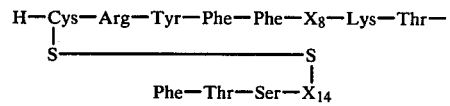

its linear precursor or a non-toxic acid addition salt thereof, in which:

$X_8$ is L-Trp or D-Trp;

and $X_{14}$ is Cys or D-Cys.

3. A polypeptide of claim 1 of the formula:

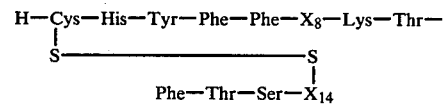

its linear precursor or a non-toxic acid addition salt thereof, in which:

$X_8$ is L-Trp or D-Trp;

and $X_{14}$ is Cys or D-Cys.

4. The polypeptide of claim 2 which is L-cysteinyl-L-arginyl-L-tyrosyl-L-phenylalanyl-L-phenylalanyl-D-tryptophyl-L-lysyl-L-threonyl-L-phenylalanyl-L-threonyl-L-seryl-L-cysteine or a non-toxic acid addition salt thereof.

5. The polypeptide of claim 2 which is L-cysteinyl-L-histidyl-L-tyrosyl-L-phenylalanyl-L-phenylalanyl-D-tryptophyl-L-lysyl-L-threonyl-L-phenylalanyl-L-threonyl-L-seryl-L-cysteine (cyclic 1,12 disulfide) or a non-toxic acid addition salt thereof.

6. The peptido resin which is tert-butyloxycarbonyl-S-p-methoxybenzyl-L-cysteinyl-$N^{im}$-tosyl-L-histidyl-O-2,6-dichlorobenzyl-L-tyrosyl-L-phenylalanyl-L-phenylalanyl-D-tryptophyl-$N^{\epsilon}$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl polystyrene ester or a non-toxic acid addition salt thereof.

7. The peptido resin which is tert-butyloxycarbonyl-S-p-methoxybenzyl-L-cysteinyl-$N^g$-tosyl-L-arginyl-O-2,6-dichlorobenzyl-L-tyrosyl-L-phenylalanyl-L-phenylalanyl-D-tryptophyl-$N^{\epsilon}$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethylpolystyrene or a non-toxic acid addition salt thereof.

* * * * *

UNITED STATES PATENT OFFICE
CERTIFICATE OF CORRECTION

Patent No. 4,209,426    Dated June 24, 1980

Inventor(s) Dimitrios Sarantakis

It is certified that error appears in the above-identified patent and that said Letters Patent are hereby corrected as shown below:

Column 4, line 33, delete "Ag3" and insert --AG3--;

Column 6, line 35, after "cysteine" insert --(cyclic 1,12-disulfide)--;

Column 6, line 37, delete "2" and insert --3--;

Signed and Sealed this

Twenty-eighth Day of October 1980

[SEAL]

Attest:

SIDNEY A. DIAMOND

Attesting Officer

Commissioner of Patents and Trademark